(12) United States Patent
Esposito et al.

(10) Patent No.: US 12,367,965 B2
(45) Date of Patent: Jul. 22, 2025

(54) WORKSTATION INTEGRATING MULTIPLE DISTINCT COMPUTING SYSTEMS

(71) Applicant: Dextro Imaging Solutions, LLC, Brandon, FL (US)

(72) Inventors: Michael B. Esposito, Brandon, FL (US); Felix Garcia, Brandon, FL (US)

(73) Assignee: Dextro Imaging Solutions, LLC, Brandon, FL (US)

( * ) Notice: Subject to any disclaimer, the term of this patent is extended or adjusted under 35 U.S.C. 154(b) by 265 days.

(21) Appl. No.: 17/683,229

(22) Filed: Feb. 28, 2022

(65) Prior Publication Data

US 2022/0367037 A1 Nov. 17, 2022

Related U.S. Application Data

(60) Provisional application No. 63/187,360, filed on May 11, 2021.

(51) Int. Cl.
*G16H 30/40* (2018.01)
*G16H 30/20* (2018.01)
(Continued)

(52) U.S. Cl.
CPC ............ *G16H 30/40* (2018.01); *G16H 30/20* (2018.01); *G06F 1/181* (2013.01); *G06F 3/0482* (2013.01)

(58) Field of Classification Search
CPC ........ G16H 30/40; G16H 30/20; G16H 40/67; G06F 1/181; G06F 3/0482; G06F 3/04842
(Continued)

(56) References Cited

U.S. PATENT DOCUMENTS 8,504,588 B2 * 8/2013 Hirschbeck ............ G16H 50/70
707/791
8,553,951 B2 * 10/2013 Kariathungal ......... G16H 30/20
382/128
(Continued)

OTHER PUBLICATIONS

Smith, Availability analysis of blade server systems, 2008, IBM Systems Journal, vol. 47, No. 4, pp. 621-640 (Year: 2008) (Year: 2008).*
(Continued)

*Primary Examiner* — Kambiz Abdi
*Assistant Examiner* — Tran N Nguyen
(74) *Attorney, Agent, or Firm* — Perilla Knox & Hildebrandt LLP; James J. Rha

(57) ABSTRACT

Disclosed herein are various examples of a workstation that integrates multiple distinct computer systems in a single chassis. A first blade computing device of a plurality of blade computing devices can receive a selection of a medical image study in a user interface. The first blade computing device can determine whether the medical image study is compatible with the first blade computing device. In response to determining that the medical image study is incompatible with the first blade computing device, the first blade computing device can identify a second blade computing device of the plurality of blade computing device with which the medical image study is compatible. The first blade computing device can generate a command to activate the second blade computing device and to access the medical image study and provide the command to the switching device.

20 Claims, 5 Drawing Sheets

(51) Int. Cl.
　　　*G06F 1/18*　　　　(2006.01)
　　　*G06F 3/0482*　　(2013.01)
(58) Field of Classification Search
　　　USPC .......................................................... 705/2–3
　　　See application file for complete search history.

(56) References Cited

U.S. PATENT DOCUMENTS

| | | | |
|---|---|---|---|
| 8,826,069 B2* | 9/2014 | Krishnamurthy ... | G06F 11/2007 |
| | | | 714/11 |
| 9,576,140 B1* | 2/2017 | Ghostine ............... | H04L 9/3213 |
| 11,544,407 B1* | 1/2023 | Sjöstrand .............. | G06F 3/0486 |
| 2007/0186106 A1* | 8/2007 | Ting .................... | H04L 63/0815 |
| | | | 713/168 |
| 2017/0358047 A1* | 12/2017 | Esposito ............ | G06Q 10/0631 |
| 2020/0045754 A1* | 2/2020 | Kamgaing ........... | H01Q 1/2266 |
| 2021/0249117 A1* | 8/2021 | Pan ........................ | G16H 30/40 |

OTHER PUBLICATIONS

Screen captures from YouTube video clip entitled "MyChart: Connecting Accounts (For Mobile Devices)," 1 pages, uploaded on 2021 by user "Epic". Retrieved from Internet: <https://youtu.be/4U4z9FHjcY4?si=unur7rNBit62DCo1> (Year: 2021).*

Smith, Availability analysis of blade server systems, 2008, IBM Systems Journal, vol. 47, No. 4, pp. 621-640 (Year: 2008).*

* cited by examiner

WORKSTATION INTEGRATING MULTIPLE DISTINCT COMPUTING SYSTEMS

CROSS-REFERENCE TO RELATED APPLICATIONS

This application claims the benefit of, and priority to, U.S. Provisional Application No. 63/187,360, filed May 11, 2021, and entitled "WORKSTATION INTEGRATING MULTIPLE DISTINCT COMPUTING SYSTEM," which is incorporated herein by reference in its entirety.

BACKGROUND

Many modalities, or methods, exist for the creation of images to be used in medical diagnosis and treatment. These modalities include radiography, or X-ray imaging, computed tomography (CT), magnetic resonance imaging (MRI), ultrasound, mammography, nuclear medicine, positron emission tomography (PET), and other modalities. The images produced as a result of these modalities are carefully examined by specialists having advanced training, such as radiologists.

In recent years, digital technology has made possible a shift from hard copy distribution of medical images for examination to digital distribution. Digital distribution of medical images is typically performed by picture archiving and communications systems (PACS). PACS comprise computers or networks dedicated to the storage, retrieval, distribution, and presentation of medical images. The medical images are stored in a format such as the digital imaging and communications in medicine (DICOM) standard. The use of PACS has also enabled teleradiology, whereby a radiologist or other specialist may examine a medical image and associated patient data at an off-site location.

BRIEF DESCRIPTION OF THE DRAWINGS

Many aspects of the present disclosure can be better understood with reference to the following drawings. The components in the drawings are not necessarily to scale, with emphasis instead being placed upon clearly illustrating the principles of the disclosure. Moreover, in the drawings, like reference numerals designate corresponding parts throughout the several views.

DETAILED DESCRIPTION

Figure 1:
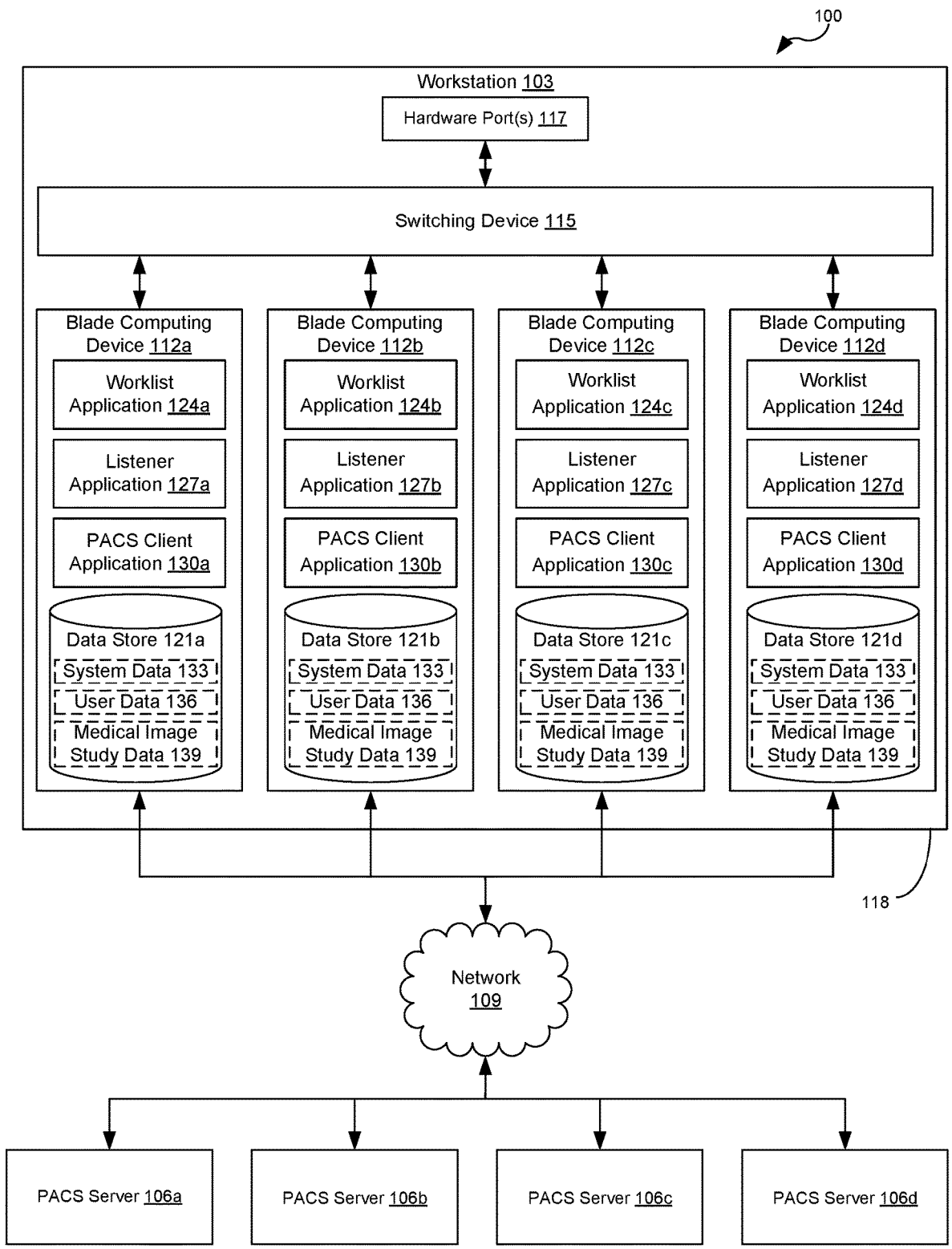
FIG. 1 is a schematic block diagram of a networked environment according to various embodiments of the present disclosure.

The present disclosure relates to a workstation that integrates multiple distinct computer systems in a single chassis. There are several different PACS platforms on the market, and they do not interoperate with each other. Although a hospital may standardize on a single PACS platform, different hospitals may use different PACS systems. Even if two hospitals were to use the same PACS software, they would use different data warehouses for the PACS data, which makes it impossible for a single PACS client instance to communicate with the PACS servers associated with the two hospitals.

Due to the nature of the practice, many radiologists or other specialists may perform work for multiple hospitals, outpatient imaging centers, clinics, and so on, each of which may use distinct PACS platforms. Unfortunately, it is not a simple matter to run distinct PACS clients on an individual machine. For example, a first PACS client may need to connect to a first hospital's virtual private network (VPN), and once that VPN connection is established, a second PACS client cannot at the same time connect to a VPN of a second hospital. Generally, the PACS clients require exclusive access to computer workstation resources when they are executing.

With these constraints, some radiologists or other specialists may choose to have multiple independent computer systems, one for each PACS platform that they use, so that they can quickly switch among the systems. However, this is cumbersome and takes up a great deal of office work area. Generally, a workstation will have four or more monitors, including two diagnostic monitors, a worklist monitor, and a dictation monitor. Multiplying four monitors by how ever many PACS systems quickly becomes unsustainable. Further, diagnostic monitors with the capability of viewing mammography or other modalities can be very expensive (e.g., five megapixel specialty monitors).

Keyboard-video-mouse (KVM) switches are another option, which allow multiple workstations to share the same keyboard, monitor, and mouse. However, conventional KVM switches are not designed for medical use or the associated high specifications for video, and they do not allow for the seamless switching of microphone inputs required for dictation. Virtualization of separate systems is not practical due to the high resolution requirements and not being able to seamlessly physically switch inputs such as USB inputs or microphone inputs.

Various embodiments of the present disclosure introduce a workstation that indicates multiple distinct computer systems in a single chassis. For example, the single chassis may include a plurality of blade systems (e.g., two, four, or more), each of which is configured for a distinct PACS platform with separately executing operating systems. Thus, each of the systems can connect to distinct VPNs simultaneously, and the PACS clients are able to exclusively control operating system resources without running into interference with one another. This bridges issues with dictation, software compatibility, separate data sources, and network connectivity that prevent multiple PACS clients from executing simultaneously under a single operating system. At the same time, Food and Drug Administration (FDA) compliance is maintained, with the ability to meet resolution quality and calibration ability that is impossible for virtualized systems. In addition to medical imaging, the workstation may have applications within fire departments and emergency medical services systems, which may similarly need to communicate with disparate systems that cannot interoperate under a single operating system.

FIG. 1 shows a networked environment 100 according to various embodiments. The networked environment 100 can include a workstation 103 and a plurality of PACS servers 106a-d in communication over a network 109. The network 109 can include, for example, the Internet, intranets, extranets, wide area networks (WANs), local area networks (LANs), wired networks, wireless networks, cable networks, satellite networks, or other suitable networks, etc., or any combination of two or more such networks.

The workstation 103 can include a plurality of blade computing devices 112a-d, a switching device 115, and one or more hardware ports 117 included in a single chassis 118. Each blade computing device 112 can be associated with a single hospital, medical practice, or other medical provider. Each of the blade computing devices 112a-d can therefore be configured for a distinct PACS platform associated with a single medical provider and therefore associated with a particular one of the PACS servers 106. Likewise, each blade computing device 112 can operate independently of the other blade computing devices. For example, each blade computing device 112 can include a separately executing operating system, a separate network connection, and other separate components. Thus, the blade computing devices 112a-d can simultaneously connect to distinct VPNs associated with different PACS servers 106, and the applications executing on each blade computing device 112 can exclusively control operating system resources without interfering with one another. The workstation 103 can also include an internal network to allow individual blade computing devices 112a-d to communicate with each other.

In some embodiments, the blade computing devices 112a-d can be powered by multiple power supplies. Thus, if one power supply fails, one or more of the blade computing devices 112a-d can still be operable. For example, the blade computing devices 112a-d can be powered by dual 1000-watt power supplies.

Each of the blade computing devices 112a-d can comprise, for example, a server computer or any other system providing computing capability. Alternatively, each of the blade computing devices 112a-d can employ a plurality of computing devices that may be arranged, for example, in one or more server banks or computer banks or other arrangements. Such computing devices may be located in a single installation or may be distributed among many different geographical locations. For example, each of the blade computing devices 112a-d can be located in a single installation or can be distributed among many different geographical locations. For example, each of the blade computing devices 112a-d can include a plurality of computing devices that together may comprise a hosted computing resource, a grid computing resource, and/or any other distributed computing arrangement. In some cases, each of the blade computing devices 112a-d can correspond to an elastic computing resource where the allotted capacity of processing, network, storage, or other computing-related resources may vary over time.

Various applications and/or other functionality can be executed in each of the blade computing devices. Also, various data can be stored in data stores 121a-d that are accessible to each of the blade computing devices. Each data store 121a-d can be representative of a plurality of data stores as can be appreciated. The data stored in each data store 121, for example, can be associated with the operation of the various applications and/or functional entities described below.

The components executed on the blade computing devices 112a-d can include, for example, worklist applications 124a-d, listener applications 127a-d, PACS client applications 130a-d, and other applications, services, processes, systems, engines, or functionality not discussed in detail herein.

A worklist application 124 can provide switching functionality among the blade computing devices 112. The worklist application 124 executing on one of the blade computing devices 112a-d may call an application programming interface (API) specific to this specialized hardware to switch to or activate another of the blade computing devices 112. The switched-to blade computing device 112 can then become active, and thus input signals from hardware peripherals connected to the hardware ports 117 can be routed to the newly active blade computing device 112. Likewise, output signals from the newly active blade computing device 112 can be routed to hardware peripherals connected to the hardware ports 117 as appropriate.

The switching functionality of the worklist application 124 can be initiated automatically or at the direction of a user. For example, a user may click on or otherwise select a medical image study in a worklist and the workstation 103 will automatically switch to the particular blade computing device 112 with a PACS client application 130 that is capable of accessing that medical image study. In some examples, a voice command to access a particular medical image study may cause the workstation 103 to switch or activate to the appropriate blade computing device 112. Once switched, the user can dictate into a dictation system for that PACS client application 130 without switching to another headset, microphone, or other peripheral. In addition, a user interface may be provided for a user to manually switch between the blade computing devices.

The worklist application 124 can receive data associated with a medical image study over the network 109. When the worklist application 124 receives data associated with a medical image study, the worklist application 124 can assign a token to that study corresponding to the medical provider, PACS platform, or PACS server 106 associated with that medical image study. Thus, when that study is selected, the worklist application 124 can cause the appropriate blade computing device 112 to be switched to and that study to be accessed. The worklist application 124 can also store the data associated with that medical image study along with the token in the medical image study data 139.

In some examples, the worklist application 124 can send a command to the switching device 115 comprising instructions to access the medical image study and to cause the workstation 103 to switch to or activate the blade computing device 112 associated with that medical image study. In other examples, the worklist application 124 can send the command directly to the appropriate blade computing device 112. The worklist application 124 can inspect the token included with the command to determine the blade computing device 112 for which the command is intended.

Each blade computing device 112 can include one or more listener applications 127. A listener application 127 can respond to commands received from the switching device 115 or another blade computing device 112. When the listener application 127 receives a command, the listener application 127 can cause the workstation 103 to switch to or activate the blade computing device 112 associated with the listener application 127. Likewise, the listener application 127 can cause the PACS client application 130 to access the corresponding medical image study. In some examples, though, a separate application can perform each of these respective actions.

The PACS client application 130 can interface with the PACS server 106 to retrieve, view, or modify DICOM images or other data associated with medical image studies from the medical study data. Each PACS client application 130 can be associated with a distinct hospital, medical practice, or other medical provider. In some examples, to interface with the PACS server 106, the PACS client application 130 can connect to a VPN of a medical provider associated with that PACS server 106. This connection can be maintained even when the corresponding blade computing device 112 is not active. Likewise, a VPN connection can be maintained when the PACS client application 130 of a different blade computing device 112 is connected to the VPN of a different medical provider.

The PACS client application 130 can be called by the worklist application 124 when a user selects a medical image study or by the listening application when a command is received from the switching device 115. The PACS client application 130 can then access data associated with the medical image study from the medical image study data 139 and access the medical image study. The PACS client application 130 can then cause the data associated with the medical image study to be displayed via the switching device 115 on any display devices connected to the hardware ports 117. The PACS client application 130 can cause the medical image study to be displayed at a correct resolution when the workstation 103 switches between blade computing devices.

In some examples, when a particular medical image study is being accessed, the PACS client application 130 can "lock out" any monitors or other output devices connected to the workstation 103 that are not associated with that particular medical image study. This can prevent a user of the workstation 103 from accessing medical image studies associated with a different provider than the particular medical image study. The worklist application 124 can still update worklists 203*a-d* associated with those other providers, however.

The data stored in the data stores 121*a-d* can include, for example, system data 133, user data 136, medical image study data 139, and potentially other data. In some examples, the data stored in the data store 121 of each blade computing device 112 can be accessible to the other blade computing devices. In other examples, however, a single data store 121 may be accessible to all of the blade computing devices. System data 133 can contain data relating to system configurations, such as settings used to interface with a PACS server 106 and other data. User data 136 can contain data relating to users, such as schedules, locations, preferences, security credentials, and other data. The medical image study data 139 can include data associated with one or more medical image studies, including DICOM image, tokens corresponding to individual medical image studies, and other data. The medical image study data 139 can be accessed by the PACS client application 130 to access a corresponding medical image study.

The switching device 115 can facilitate switching between the blade computing devices 112. Unlike conventional KVMs or other switching devices 115, the switching device 115 can keep the hardware of a blade computing device 112 operational even when that blade computing device 112 is not active. The switching device 115 can allow the blade computing devices 112*a-d* to share resources. For example, the switching device 115 can allow the blade computing devices 112*a-d* to share hardware peripherals through the hardware ports 117.

The switching device 115 can receive a command from the worklist application 124. The switching device 115 can then forward the command to an appropriate blade computing device 112. In some examples, the command can specify a blade computing device 112 to which the command should be forwarded. In other examples, the switch can inspect the token to determine which of the blade computing devices 112*a-d* to which the command should be forwarded.

To switch the workstation 103 to a blade computing device 112, the switching device 115 can route any output signals from the blade computing device 112 to any corresponding hardware peripherals connected to the hardware ports 117. For example, the switching device 115 can route visual output from the blade computing device 112 to one or more monitors connected to the hardware ports 117. Likewise, the switching device 115 can route any input signals from hardware peripherals connected to the hardware ports 117 to the blade computing device 112. For example, the switching device 115 can route input from a mouse, keyboard, or microphone to the active blade computing device 112.

The single chassis 118 can be any housing suitable for containing the plurality of blade computing devices 112*a-d* and switching device 115 in an operable state. In some examples, the single chassis 118 can be a mobile chassis, with one or more diagnostic monitors included in the hardened, mobile chassis. The single chassis 118 can further include multiple hardware ports 117 that can be internally switched to individual blade computing devices. This can allow a same set of hardware peripherals to be used on each of the blade computing devices. In one embodiment, the single chassis 118 can have four or more monitor outputs, where the monitor outputs are internally switched to four or more video outputs of each of the blade computing devices. Likewise, a set of universal serial bus (USB) ports may be provided on the chassis, such that they are internally switched to connect to whichever of the blade computing devices 112*a-d* is currently active. Similarly, a microphone input, a keyboard input, a mouse input, or any other form of hardware input may also be internally switched.

The PACS server 106 can provide images and other data associated with a medical image study. Each PACS server 106 can be associated with a distinct hospital, medical practice, or other medical provider. The PACS server 106 can provide medical images of patients of that medical provider for any modality, such as radiography, or X-ray imaging, computed tomography, magnetic resonance imaging, ultrasound, mammography, nuclear medicine, positron emission tomography, and/or other modalities. The PACS server 106 can provide medical images in, for example, a DICOM format. The PACS server 106 can receive user input to describe the acquired medical images by way of input devices and/or clients over a data communications network. The PACS server 106 may be capable of exchanging patient-related information over a data communications network such as network through, for example, a Health Level 7 (HL7) interface.

Figure 2:
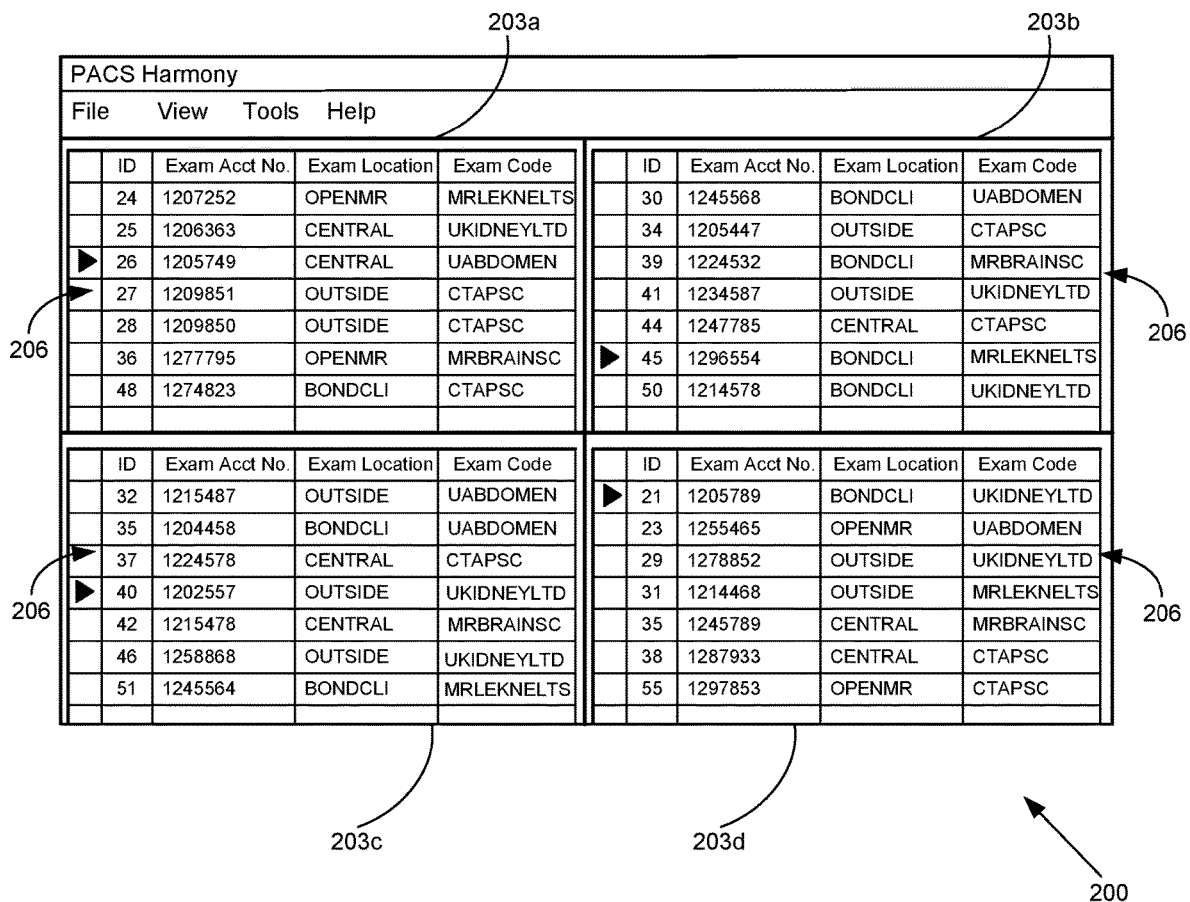
FIG. 2 is a drawing of an example worklist user interface according to various embodiments of the present disclosure.

Referring next to FIG. 2, shown is an example of a worklist user interface 200 in an embodiment of the worklist application 124. The worklist user interface 200 can enable a user of the workstation 103 to view worklists 203*a-d* generated from assignments of medical image studies. In some examples, the worklist application 124 can ensure that the worklist user interface 200 is always displayed on at least one display device connected to the hardware ports 117 while the worklist application 124 is running, unless a user takes some action to hide, minimize, or close the worklist user interface 200.

In this example, a worklist user interface 200 can have a title bar with the title "PACS Harmony," although any appropriate title may be used. The worklist user interface 200 may have a menu with any number of menus and submenus as appropriate to select features of the worklist application 124.

The worklist user interface 200 can include a plurality of separate worklists 203a-d arranged in a split-screen fashion. Each of these worklists 203a-d can correspond to a different PACS server 106 associated with a different medical provider and, by extension, to a blade computing device 112 configured to use that PACS server 106. Other arrangements of the separate worklists 203a-d can be used, however. For example, the worklist user interface 200 can instead include a plurality of tabs, with each tab displaying a different one of the separate worklists 203a-d when selected.

Each worklist 203 in the worklist user interface 200 can include a plurality of table rows 206 that provide the data associated with an instance of the given columns. In this case, table row 206 displays the data associated with a particular medical image study. A table row 206 may be selectable and modifiable by a user, depending on proper user permissions and privileges. In particular, the status may be modifiable.

In some examples, selecting a table row 206 by, for example, clicking on or performing another input action on the table row can cause the worklist application 124 to launch the PACS client application 130 to display the selected medical image study. If the selected medical image study can be accessed by the active blade computing device 112, the PACS client application 130 on that blade computing device 112 can be launched to access the medical image study. If the selected medical image study can only be accessed by a blade computing device 112 other than the active blade computing device 112, however, the workstation 103 can switch to that blade computing device 112. The PACS client application 130 on that blade computing device 112 can then be launched to access the medical image study.

Figure 3:
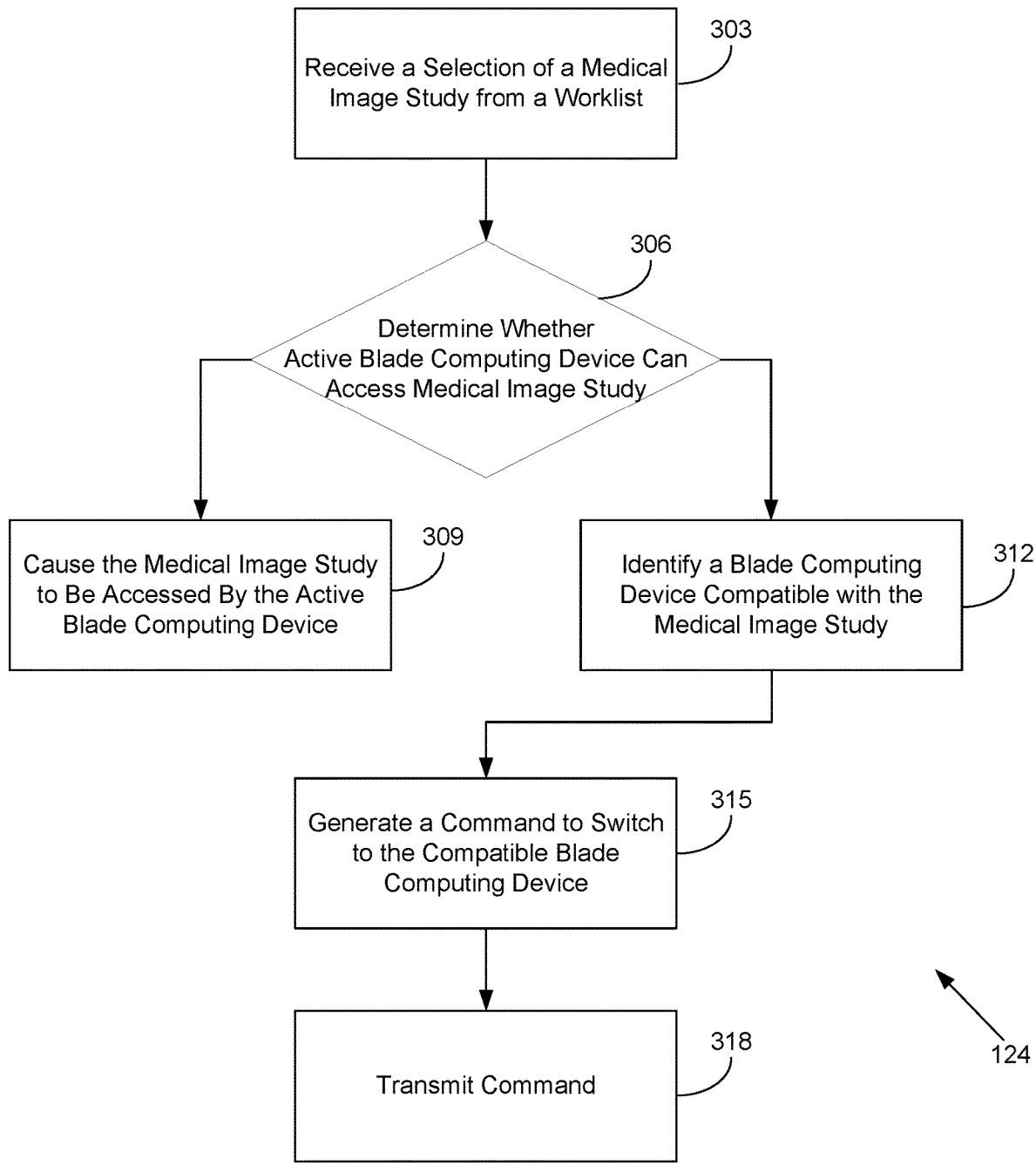
FIG. 3 is a flowchart illustrating one example of functionality implemented as a portion of a worklist application in the networked environment of FIG. 1 according to various embodiments of the present disclosure.

FIG. 3 shows an example of a flowchart that provides one example of the operation of a portion of the worklist application 124 according to various embodiments. It is understood that the flowchart of FIG. 3 provides merely an example of the many different types of functional arrangements that may be employed to implement the operation of the portion of the worklist application 124 as described herein. As an alternative, the flowchart of FIG. 3 may be viewed as depicting an example of elements of a method implemented in a blade computing device 112 according to one or more embodiments.

At step 303, the worklist application 124 can receive a selection of a medical image study. For example, a user can select the medical image study from a worklist 203 in the worklist user interface 200.

At step 306, the worklist application 124 can determine whether the currently active blade computing device 112 is capable of accessing the medical image study. For example, the worklist application 124 can check a token associated with the medical image study. That token can include an indication of a blade computing device 112 with which the medical image study is compatible or a PACS server 106 from which the medical image study originated. If the active blade computing system 112 is the one indicated by the token, or if the active blade computing device 112 is associated with the PACS server 106 indicated by the token, the active blade computing device 112 can be compatible with that medical image study. If the currently active blade computing device 112 is not compatible with the medical image study, execution can proceed to step 309. Otherwise, execution can proceed to step 312.

At step 309, if the currently active blade computing device 112 is capable of accessing the medical image study, the worklist application 124 can cause the medical image study to be accessed by the active blade computing device 112. For example, the worklist application 124 can call an API to launch the PACS client application 130. The PACS client application 130 can access data associated with that medical image study from the medical image study data 139. The PACS client application 130 can then cause medical images or other data associated the medical image study to be displayed on one or more display devices connected to the hardware ports 117 of the workstation 103.

At step 312, if the currently active blade computing device 112 is incapable of accessing the medical image study, the worklist application 124 can identify a blade computing device 112 that is compatible with the medical image study. In other words, the worklist application 124 can identify a blade computing device 112 that is capable of accessing the medical image study. For example, the worklist application 124 can determine which PACS server 106 is associated with that medical study. The worklist application 124 can then identify the blade computing device 112 that is associated with that PACS server 106.

At step 315, the worklist application can generate a command to cause the workstation 103 to switch to or activate the blade computing device 112 and to access the medical image study. In some examples, the command can include the medical image study itself, a token associated with that study, or both.

At step 318, the worklist application 124 can transmit the command to an appropriate destination. In some examples, the worklist application 124 can transmit the command to the switching device 115, which can in turn transmit the command to the appropriate blade computing device 112. In other examples, the worklist application 124 can transmit the command directly to the appropriate blade computing device 112. Thereafter, the process can proceed to completion.

Figure 4:
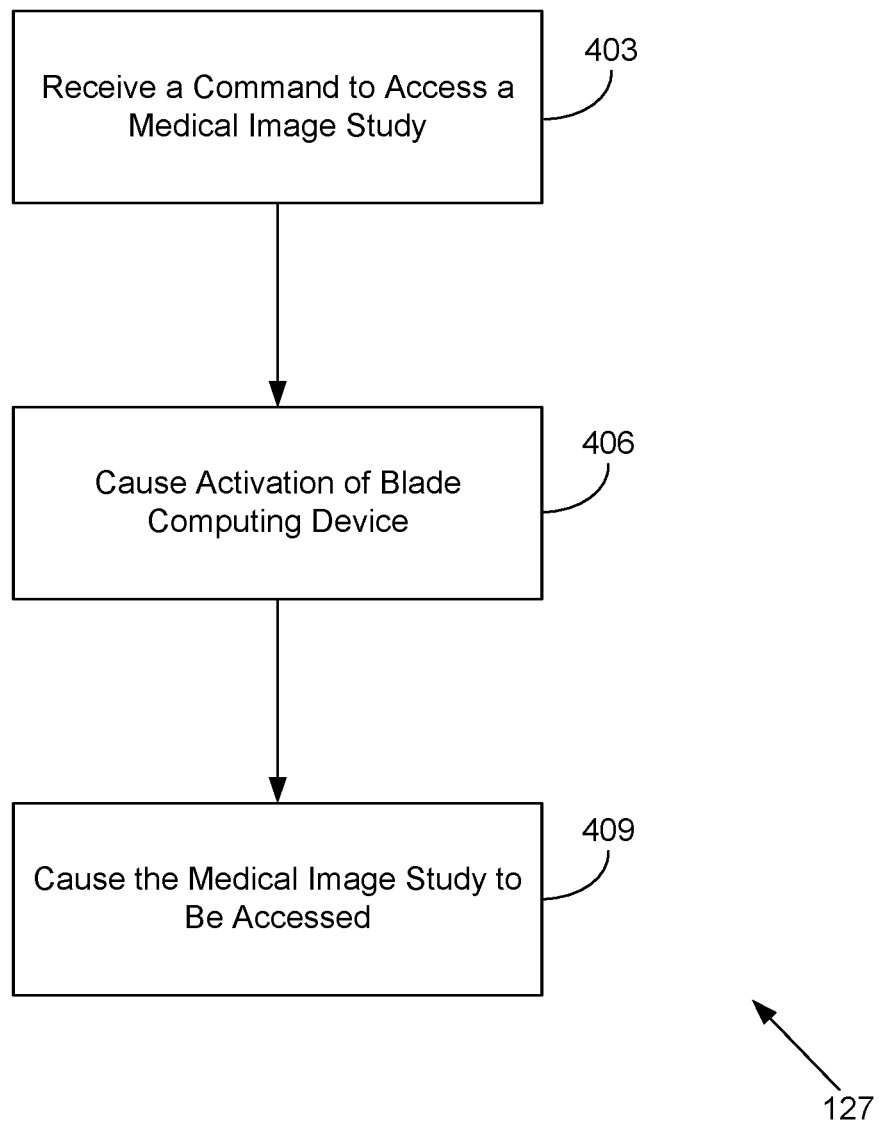
FIG. 4 is a flowchart illustrating one example of functionality implemented as a portion of a listener application in the networked environment of FIG. 1 according to various embodiments of the present disclosure.

FIG. 4 shows an example of a flowchart that provides one example of the operation of a portion of the listener application 127 according to various embodiments. It is understood that the flowchart of FIG. 4 provides merely an example of the many different types of functional arrangements that may be employed to implement the operation of the portion of the listener as described herein. As an alternative, the flowchart of FIG. 4 may be viewed as depicting an example of elements of a method implemented in a blade computing device 112 according to one or more embodiments.

At step 403, the listener application 127 can receive a command. In some examples, the command can be received from the switching device 115 after originated from another blade computing device 112. In other examples, the command can be received directly from the other blade computing device 112.

At step 406, the listener application 127 can cause the workstation 103 to switch to or activate a blade computing device 112 on which the listener application 127 is executing. In some examples, the listener can cause the switching device 115 to switch the workstation 103 to that blade computing device 112. In that case, any output signals from the newly-active blade computing device 112 can be routed by the switching device 115 to appropriate hardware peripherals connected to the hardware ports 117, and any input signals from those hardware peripherals can be routed to the newly-active blade computing device 112.

At step 409, the listener application 127 can cause the medical image study to be accessed. For example, the worklist application 124 can call an API to launch the PACS client application 130. The PACS client application 130 access data associated with that medical image study from the medical image study data 139. The PACS client application 130 can then cause medical images or other data associated the medical image study to be displayed on one or more display devices connected to the hardware ports 117 of the workstation 103. Thereafter, the process can proceed to completion.

Figure 5:
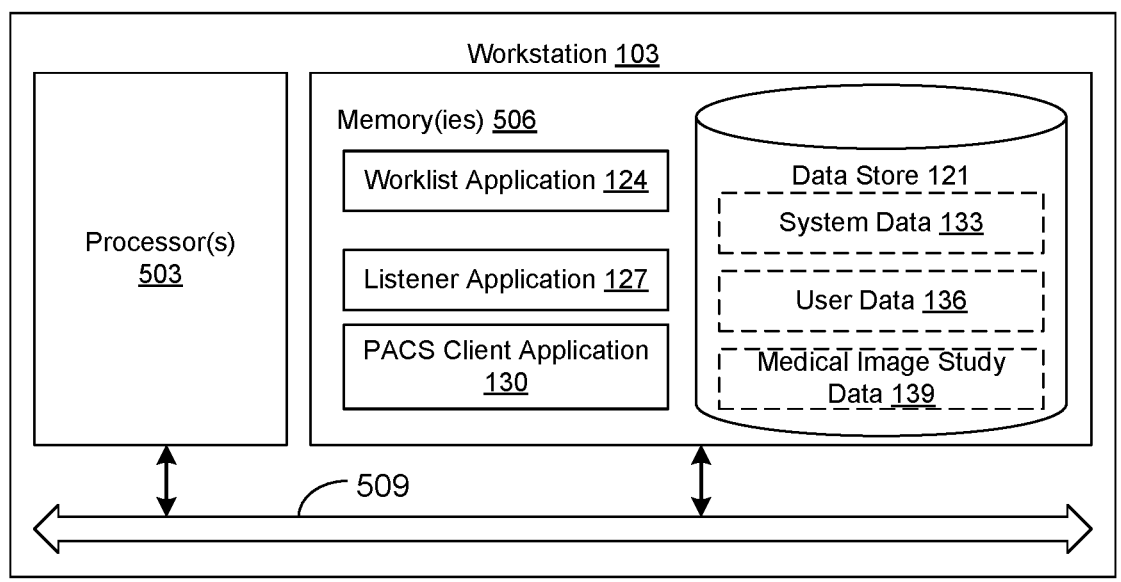
FIG. 5 is a schematic block diagram that provides one example illustration of a computing environment employed in the networked environment of FIG. 1 according to various embodiments of the present disclosure.

With reference to FIG. 5, shown is a schematic block diagram of the workstation 103 according to an embodiment of the present disclosure. The workstation 103 includes one or more computing devices 500. Each computing device 500 includes at least one processor circuit, for example, having a processor 503 and a memory 506, both of which are coupled to a local interface 509. To this end, each computing device 500 may comprise, for example, at least one server computer or like device. The local interface 509 may comprise, for example, a data bus with an accompanying address/control bus or other bus structure as can be appreciated.

Stored in the memory 506 are both data and several components that are executable by the processor 503. In particular, stored in the memory 506 and executable by the processor 503 are the worklist application 124, the listener application 127, the PACS client application 130, and potentially other applications. Also stored in the memory 506 may be a data store 121 and other data. Stored in the data store can by system data 133, user data 136, medical image study data 139, and potentially other data. In addition, an operating system may be stored in the memory 506 and executable by the processor 503.

It is understood that there may be other applications that are stored in the memory 506 and are executable by the processor 503 as can be appreciated. Where any component discussed herein is implemented in the form of software, any one of a number of programming languages may be employed such as, for example, C, C++, C#, Objective C, Java®, JavaScript®, Perl, PHP, Visual Basic®, Python®, Ruby, Flash®, or other programming languages.

A number of software components are stored in the memory 506 and are executable by the processor 503. In this respect, the term "executable" means a program file that is in a form that can ultimately be run by the processor 503. Examples of executable programs may be, for example, a compiled program that can be translated into machine code in a format that can be loaded into a random access portion of the memory 506 and run by the processor 503, source code that may be expressed in proper format such as object code that is capable of being loaded into a random access portion of the memory 506 and executed by the processor 503, or source code that may be interpreted by another executable program to generate instructions in a random access portion of the memory 506 to be executed by the processor 503, etc. An executable program may be stored in any portion or component of the memory 506 including, for example, random access memory (RAM), read-only memory (ROM), hard drive, solid-state drive, USB flash drive, memory card, optical disc such as compact disc (CD) or digital versatile disc (DVD), floppy disk, magnetic tape, or other memory components.

The memory 506 is defined herein as including both volatile and nonvolatile memory and data storage components. Volatile components are those that do not retain data values upon loss of power. Nonvolatile components are those that retain data upon a loss of power. Thus, the memory 506 may comprise, for example, random access memory (RAM), read-only memory (ROM), hard disk drives, solid-state drives, USB flash drives, memory cards accessed via a memory card reader, floppy disks accessed via an associated floppy disk drive, optical discs accessed via an optical disc drive, magnetic tapes accessed via an appropriate tape drive, and/or other memory components, or a combination of any two or more of these memory components. In addition, the RAM may comprise, for example, static random access memory (SRAM), dynamic random access memory (DRAM), or magnetic random access memory (MRAM) and other such devices. The ROM may comprise, for example, a programmable read-only memory (PROM), an erasable programmable read-only memory (EPROM), an electrically erasable programmable read-only memory (EEPROM), or other like memory device.

Also, the processor 503 may represent multiple processors 503 and/or multiple processor cores and the memory 506 may represent multiple memories 506 that operate in parallel processing circuits, respectively. In such a case, the local interface 509 may be an appropriate network that facilitates communication between any two of the multiple processors 503, between any processor 503 and any of the memories 506, or between any two of the memories 506, etc. The local interface 509 may comprise additional systems designed to coordinate this communication, including, for example, performing load balancing. The processor 503 may be of electrical or of some other available construction.

Although the worklist application 124, the listener application 127, the PACS client application 130, and other various systems described herein may be embodied in software or code executed by general purpose hardware as discussed above, as an alternative the same may also be embodied in dedicated hardware or a combination of software/general purpose hardware and dedicated hardware. If embodied in dedicated hardware, each can be implemented as a circuit or state machine that employs any one of or a combination of a number of technologies. These technologies may include, but are not limited to, discrete logic circuits having logic gates for implementing various logic functions upon an application of one or more data signals, application specific integrated circuits (ASICs) having appropriate logic gates, field-programmable gate arrays (FPGAs), or other components, etc. Such technologies are generally well known by those skilled in the art and, consequently, are not described in detail herein.

The flowcharts of FIGS. 3-4 show the functionality and operation of an implementation of portions of the worklist application 124 and the listener application 127. If embodied in software, each block may represent a module, segment, or portion of code that comprises program instructions to implement the specified logical function(s). The program instructions may be embodied in the form of source code that comprises human-readable statements written in a programming language or machine code that comprises numerical instructions recognizable by a suitable execution system such as a processor 503 in a computer system or other system. The machine code may be converted from the source code, etc. If embodied in hardware, each block may represent a circuit or a number of interconnected circuits to implement the specified logical function(s).

Although the flowcharts of FIGS. 3-4 show a specific order of execution, it is understood that the order of execution may differ from that which is depicted. For example, the order of execution of two or more blocks may be scrambled relative to the order shown. Also, two or more blocks shown in succession in FIGS. 3-4 may be executed concurrently or with partial concurrence. Further, in some embodiments, one or more of the blocks shown in FIGS. 3-4 may be skipped or omitted. In addition, any number of counters, state variables, warning semaphores, or messages might be added to the logical flow described herein, for purposes of enhanced utility, accounting, performance measurement, or providing troubleshooting aids, etc. It is understood that all such variations are within the scope of the present disclosure.

Also, any logic or application described herein, including the worklist application 124, the listener application 127, and the PACS client application 130, that comprises software or code can be embodied in any non-transitory computer-readable medium for use by or in connection with an instruction execution system such as, for example, a processor 503 in a computer system or other system. In this sense, the logic may comprise, for example, statements including instructions and declarations that can be fetched from the computer-readable medium and executed by the instruction execution system. In the context of the present disclosure, a "computer-readable medium" can be any medium that can contain, store, or maintain the logic or application described herein for use by or in connection with the instruction execution system.

The computer-readable medium can comprise any one of many physical media such as, for example, magnetic, optical, or semiconductor media. More specific examples of a suitable computer-readable medium would include, but are not limited to, magnetic tapes, magnetic floppy diskettes, magnetic hard drives, memory cards, solid-state drives, USB flash drives, or optical discs. Also, the computer-readable medium may be a random access memory (RAM) including, for example, static random access memory (SRAM) and dynamic random access memory (DRAM), or magnetic random access memory (MRAM). In addition, the computer-readable medium may be a read-only memory (ROM), a programmable read-only memory (PROM), an erasable programmable read-only memory (EPROM), an electrically erasable programmable read-only memory (EEPROM), or other type of memory device.

Further, any logic or application described herein, including the worklist application 124, the listener application 127, and the PACS client application 130, may be implemented and structured in a variety of ways. For example, one or more applications described may be implemented as modules or components of a single application. Further, one or more applications described herein may be executed in shared or separate computing devices or a combination thereof. For example, a plurality of the applications described herein may execute in the same computing device 500, or in multiple computing devices 500 in the same workstation 103.

A phrase, such as "at least one of X, Y, or Z," unless specifically stated otherwise, is to be understood with the context as used in general to present that an item, term, etc., can be either X, Y, or Z, or any combination thereof (e.g., X, Y, and/or Z). Similarly, "at least one of X, Y, and Z," unless specifically stated otherwise, is to be understood to present that an item, term, etc., can be either X, Y, and Z, or any combination thereof (e.g., X, Y, and/or Z). Thus, as used herein, such phrases are not generally intended to, and should not, imply that certain embodiments require at least one of either X, Y, or Z to be present, but not, for example, one X and one Y. Further, such phrases should not imply that certain embodiments require each of at least one of X, at least one of Y, and at least one of Z to be present.

Although embodiments have been described herein in detail, the descriptions are by way of example. The features of the embodiments described herein are representative and, in alternative embodiments, certain features and elements may be added or omitted. Additionally, modifications to aspects of the embodiments described herein may be made by those skilled in the art without departing from the spirit and scope of the present disclosure defined in the following claims, the scope of which are to be accorded the broadest interpretation so as to encompass modifications and equivalent structures.

The invention claimed is:

1. A computing system, comprising:
   a first blade computing device comprising at least one processor and at least one memory, the at least one memory having processor-readable instructions stored therein;
   a second blade computing device; and
   a switching device connected to the first blade computing device and the second blade computing device and configured to facilitate activation of the first blade computing device or the second blade computing device, wherein the at least one processor is configured to access the at least one memory and execute the processor-readable instructions to perform operations, the operations comprising:
      receiving a selection of a medical image study in a user interface;
      determining whether the medical image study is accessible by the first blade computing device based at least in part on a token associated with the medical image study, the token comprising an indication of a specific blade computing device that is configurable to access the medical image study;
      identifying that the second blade computing device is configurable to access the medical image study based at least in part on the token, in response to determining that the medical image study is inaccessible by the first blade computing device; and
      generating an output signal to cause the computing system to activate the second blade computing device and for the second blade computing device to access the medical image study, the output signal being transmitted via the switching device.

2. The system of claim 1, wherein the medical image study is a first medical image study, and the processor-readable instructions, when executed, further cause the first blade computing device to at least:
   receive from the switching device a command to activate the first blade computing device and to access a second medical image study;
   cause an activation of the first blade computing device so that the active blade computing device switches to the first blade computing device from the second blade computing device; and
   access the second medical image study.

3. The system of claim 2, wherein the processor-readable instructions that cause the first blade computing device to access the second medical image study further cause the first blade computing device to at least:
   access data corresponding to the second medical image study from a data store accessible to the first blade computing device; and
   cause the data corresponding to the second medical image study to be displayed in a display accessible to the first blade computing device.

4. The system of claim 1, wherein the user interface comprises a plurality of worklists, and individual ones of the plurality of worklists comprise a plurality of medical image studies.

5. The system of claim 4, wherein the processor-readable instructions, when executed, further cause the first blade computing device to at least cause a worklist from the plurality of worklists to comprise an indication of the medical image study.

6. The system of claim 1, wherein the switching device is configured to enable sharing of one or more hardware peripherals between the first blade computing device and the second blade computing device.

7. The system of claim 1, wherein the first blade computing device is associated with a first picture archiving and communications systems (PACS) server, and the second blade computing device is associated with a second PACS server.

8. A computer-implemented method, comprising:
receiving, by one or more processors, a selection of a medical image study in a user interface;
determining, by the one or more processors, whether the medical image study is accessible by a first blade computing device based at least in part on a token associated with the medical image study, the token comprising an indication of a specific blade computing device that is configurable to access the medical image study;
identifying, by the one or more processors, that a second blade computing device is configurable to access the medical image study based at least in part on the token, in response to determining that the medical image study is inaccessible by the first blade computing device; and
generating, by the one or more processors, an output signal to cause activation of the second blade computing device and for the second blade computing device to access the medical image study, the output signal being transmitted via a switching device connected to the first blade computing device and the second blade computing device.

9. The method of claim 8, wherein the medical image study is a first medical image study, the method further comprising:
receiving, by the one or more processors, a command to activate the first blade computing device and to access a second medical image study;
causing, by the one or more processors, an activation of the first blade computing device so that the active blade computing device switches to the first blade computing device from the second blade computing device; and
accessing, by the one or more processors, the second medical image study via the first blade computing device.

10. The method of claim 9, wherein accessing the second medical image study further comprises:
accessing, by the one or more processors, data corresponding to the second medical image study from a data store accessible to the first blade computing device; and
encoding, by the one or more processors, the data corresponding to the second medical image study for rendering in a display.

11. The method of claim 8, wherein the first blade computing device is associated with a first picture archiving and communications systems (PACS) server, and the second blade computing device is associated with a second PACS server.

12. The method of claim 11, wherein the token further comprises an additional indication of a server from which the medical image study originated.

13. The method of claim 8, wherein the switching device is configured to enable sharing of one or more hardware peripherals between the first blade computing device and the second blade computing device.

14. The method of claim 8, further comprising causing, by the one or more processors, a worklist from a plurality of worklists to comprise an indication of the medical image study, individual ones of the plurality of worklists comprising a plurality of medical image studies.

15. A non-transitory computer-readable medium storing a set of instructions that, when executed by at least one processor, cause the at least one processor to perform operations comprising:
receiving, by one or more processors, a selection of a medical image study in a user interface;
determining, by the one or more processors, whether the medical image study is accessible by a first blade computing device based at least in part on a token associated with the medical image study, the token comprising an indication of a specific blade computing device that is configurable to access the medical image study;
identifying, by the one or more processors, that a second blade computing device is configurable to access the medical image study based at least in part on the token, in response to determining that the medical image study is inaccessible by the first blade computing device; and
generating, by the one or more processors, an output signal to cause activation of the second blade computing device and for the second blade computing device to access the medical image study, the output signal being transmitted via a switching device connected to the first blade computing device and the second blade computing device.

16. The non-transitory computer-readable medium of claim 15, wherein the medical image study is a first medical image study, the operations further comprising:
receiving, by the one or more processors, a command to activate the first blade computing device and to access a second medical image study;
causing, by the one or more processors, an activation of the first blade computing device so that the active blade computing device switches to the first blade computing device from the second blade computing device; and
accessing, by the one or more processors, the second medical image study via the first blade computing device.

17. The non-transitory computer-readable medium of claim 16, wherein accessing the second medical image study further comprises:
accessing, by the one or more processors, data corresponding to the second medical image study from a data store accessible to the first blade computing device; and
encoding, by the one or more processors, the data corresponding to the second medical image study for rendering in a display.

18. The non-transitory computer-readable medium of claim 15, wherein the first blade computing device is associated with a first picture archiving and communications systems (PACS) server, and the second blade computing device is associated with a second PACS server.

19. The non-transitory computer-readable medium of claim 18, wherein the token further comprises an additional indication of a server from which the medical image study originated.

20. The non-transitory computer-readable medium of claim 15, the operations further comprising:
    causing, by the one or more processors, a worklist from a plurality of worklists to comprise an indication of the medical image study, individual ones of the plurality of worklists comprising a plurality of medical image studies.

\* \* \* \* \*